United States Patent
Dowgiallo et al.

(10) Patent No.: US 11,662,318 B2
(45) Date of Patent: May 30, 2023

(54) METHODS TO DETECT TRACE LEVELS OF GENETIC MATERIALS USING COLLOIDAL GOLD NANOPARTICLES ON QUARTZ PAPER OR METAMATERIAL SUBSTRATES AND SURFACE-ENHANCED RAMAN SCATTERING

(71) Applicant: Salvo Technologies, Inc., Largo, FL (US)

(72) Inventors: Anne-Marie Dowgiallo, Tampa, FL (US); Hugh Garvey, Seminole, FL (US); John Dougherty, Pinellas Park, FL (US)

(73) Assignee: Salvo Technologies, Inc., Largo, FL (US)

( * ) Notice: Subject to any disclaimer, the term of this patent is extended or adjusted under 35 U.S.C. 154(b) by 5 days.

(21) Appl. No.: 17/376,511

(22) Filed: Jul. 15, 2021

(65) Prior Publication Data

US 2022/0026366 A1    Jan. 27, 2022

Related U.S. Application Data

(60) Provisional application No. 63/054,409, filed on Jul. 21, 2020.

(51) Int. Cl.
*G01N 21/65*     (2006.01)
*G01N 33/49*     (2006.01)
*G01N 1/28*      (2006.01)

(52) U.S. Cl.
CPC ............ *G01N 21/658* (2013.01); *G01N 1/28* (2013.01); *G01N 33/49* (2013.01)

(58) Field of Classification Search
None
See application file for complete search history.

(56) References Cited

U.S. PATENT DOCUMENTS 3,960,491 A * 6/1976 Giaever ............... G01N 33/553
                                                    436/805
6,787,366 B1 * 9/2004 Novak .................... G01N 31/22
                                                    436/166
2014/0154788 A1 * 6/2014 Omenetto ................. G01J 5/02
                                                    435/287.7
2014/0193301 A1 * 7/2014 Xiong .................... G02B 1/002
                                                    430/296
2018/0031483 A1 * 2/2018 Singamaneni ....... G01N 21/554

FOREIGN PATENT DOCUMENTS

WO    WO-2005092286 A2 * 10/2005  ........... A61K 9/0009

OTHER PUBLICATIONS

Segawa, Hiroki, et al. "Rapid detection of hypnotics using surface-enhanced Raman scattering based on gold nanoparticle co-aggregation in a wet system." Analyst 144.6 (2019): 2158-2165 (Year: 2019).*
Zhou, J. et al., "Highly selective detection of I-Phenylalanine by molecularly imprinted polymers coated Au nanoparticles via surface-enhanced Raman scattering." Talanta. May 1, 2020;211:120745. doi: 10.1016/j.talanta.2020.120745. Epub Jan. 13, 2020. PMID: 32070625 (Year: 2020).*
Stuart, D., et al. "In vivo glucose measurement by surface-enhanced Raman spectroscopy." Analytical chemistry 78.20 (2006): 7211-7215 (Year: 2006).*
Kitahama, Y., et al. "Different behaviour of molecules in dark SERS state on colloidal Ag nanoparticles estimated by truncated power law analysis of blinking SERS." Physical Chemistry Chemical Physics 17.33 (2015): 21204-21210 (Year: 2015).*
Hong, Seongmin. Optimization, Modification and Applications of Gold Nanoparticles as the Substrates of Surface Enhanced Raman Spectroscopy. University of South Florida, 2013 (Year: 2013).*
Zhang, X. et al. "Hierarchical porous plasmonic metamaterials for reproducible ultrasensitive surface-enhanced Raman spectroscopy." Advanced materials 27.6 (2015): 1090-1096 (Year: 2015).*

* cited by examiner

*Primary Examiner* — Tarifur R Chowdhury
*Assistant Examiner* — Roberto Fabian, Jr.
(74) *Attorney, Agent, or Firm* — Dennis L. Cook, Esq.

(57) ABSTRACT

The use of colloidal gold nanoparticles deposited on quartz paper or metamaterial substrates to enable trace level detection of biological materials such as genetic materials using Surface-enhanced Raman Scattering (SERS) wherein this molecule of interest may be tested in pure solutions or human blood is disclosed.

3 Claims, No Drawings

METHODS TO DETECT TRACE LEVELS OF GENETIC MATERIALS USING COLLOIDAL GOLD NANOPARTICLES ON QUARTZ PAPER OR METAMATERIAL SUBSTRATES AND SURFACE-ENHANCED RAMAN SCATTERING

CROSS-REFERENCE TO RELATED APPLICATION

The present application claims the benefit of previously filed Provisional Patent Application, Ser. No. 63/054,409 filed on Jul. 21, 2020.

FIELD OF THE INVENTION

The method of this disclosure belongs to the field of Raman Scattering spectroscopy. More specifically it is the use of colloidal gold nanoparticles deposited on quartz paper or metamaterial substrates to enhance the Surface-enhanced Raman Scattering that enables trace level detection of biological materials such as genetic materials.

BACKGROUND OF THE INVENTION

Raman spectroscopy is a form of vibrational spectroscopy, much like infrared (IR) spectroscopy. However, whereas IR bands arise from a change in the dipole moment of a molecule due to an interaction of light with the molecule, Raman bands arise from a change in the polarizability of the molecule due to the same interaction. This means that these observed bands (corresponding to specific energy transitions) arise from specific molecular vibrations. When the energies of these transitions are plotted as a spectrum, they can be used to identify the molecule as they provide a "molecular fingerprint" of the molecule being observed. Certain vibrations that are allowed in Raman are forbidden in IR, whereas other vibrations may be observed by both techniques, although at significantly different intensities, thus these techniques can be thought of as complementary.

Since the discovery of the Raman effect in 1928 by C. V. Raman and K. S. Krishnan, Raman spectroscopy has become an established, as well as a practical, method of chemical analysis and characterization applicable to many different chemical species.

Surface-enhanced Raman spectroscopy, or surface-enhanced Raman scattering (SERS), is a surface-sensitive technique that enhances Raman scattering by molecules adsorbed on rough metal surfaces or by nanostructures such as plasmonic-magnetic silica nanotubes. The enhancement factor can be as much as $10^{10}$ to $10^{11}$, which means the technique may detect single molecules. Surface-enhanced Raman scattering (SERS) is the Raman scattering from a compound (or ion) adsorbed on or even within a few Angstroms of a structured metal surface can be $10^3$-$10^6\times$ greater than in solution. This surface-enhanced Raman scattering is strongest on silver, but is observable on gold and copper as well for common excitation sources. At practical excitation wavelengths, enhancement on other metals is unimportant.

BRIEF SUMMARY OF THE INVENTION

The method of this invention uses colloidal gold nanoparticles deposited on quartz paper or metamaterial substrates to enable trace level detection of biological materials such as genetic materials using surface-enhanced Raman Scattering (SERS) wherein this molecule of interest may be tested in pure solutions or human blood.

DESCRIPTION OF THE PREFERRED EMBODIMENT

Gold nanoparticles are synthesized according to the Lee and Meisel method (Lee, P. C. and Meisel, D. "Adsorption and surface-enhanced Raman of dyes on silver and gold sols" *J. Phys. Chem.* 1982, 86, 3391-3395). In the preferred embodiment the following steps in the order presented prepare the colloidal gold nanoparticles:

1. A 250 mL Erlenmeyer flask is soaked in a base bath solution overnight.
2. The flask is rinsed with copious amounts of purified water before adding 200-300 mL of purified water and 0.05 to 0.06 grams $HAuCl_4$.
3. The lights are turned off to prevent any interaction with the gold salt.
4. The water is brought to boiling with moderate magnetic stirring on a hot plate.
5. Once boiling, the stirring is increased until a vortex is achieved in the solution.
6. Then, 0.05 to 0.06 grams sodium citrate is rapidly added to the solution, and boiling is continued with rapid stirring for 14 minutes.
7. The entire flask is removed from the hot plate, stir bar is removed, and the solution is cooled to room temperature.
8. And finally, the gold nanoparticles solution is cooled in the refrigerator overnight.

Once cooled, the gold nanoparticles are measured with absorption spectroscopy to confirm the position of the surface plasmon peak at 540 nm. The gold nanoparticles solution is centrifuged in glass test tubes at 7200 rpm for 25 minutes per batch (1 batch=12 test tubes containing approximately 42 mL of solution). The supernatant containing water and dissolved ions is discarded, whereas the pellets from all test tubes containing gold nanoparticles is pipetted and combined into a separate vial.

Analyte of interest (for example Phenylalanine for genetic materials) testing in blood on paper substrate is accomplished as follows:

1. 20-30 µL of colloidal gold nanoparticles is mixed with 20-30 µL Phenylalanine dissolved in blood at a concentration <60 mg/dL and 0.6-1 µL 20 mM sodium chloride (NaCl).
2. This is mixed well either by hand or vortex for a few seconds.
3. Then, 15-20 µL of the mixture is pipetted onto an 8 mm quartz paper circle and measured immediately with the Raman system at a power density of approximately 100 $W/cm^2$.
4. Phenylalanine could be replaced by other analytes of interest as are well known by those skilled in the art.

Analyte of interest (for example Phenylalanine for genetic materials) testing on metamaterial is accomplished as follows:

1. 20-30 µL of colloidal gold colloid nanoparticles is mixed with 20-30 µL Phenylalanine dissolved in pure solvent at a concentration <60 mg/dL and 0.6-1 µL 20 mM sodium chloride (NaCl).
2. This is mixed well either by hand or vortex for a few seconds.
3. Then, 5-10 µL of the mixture is pipetted onto 4 mm metamaterial substrate and allowed to dry before interrogating with 785 nm laser excitation and Raman instrumentation at a power density of approximately 100 W/cm$^2$.
4. Phenylalanine could be replaced by other analytes of interest as are well known by those skilled in the art.

Analyte of interest (for example Phenylalanine for genetic materials) testing on metamaterial in blood is accomplished as follows:
1. 20-30 µL of colloidal gold nanoparticles is mixed with 0.6-1 µL 20 mM NaCl and 5 µL of this mixture is pipetted onto a metamaterial substrate and allowed to dry.
2. A non-metalized porous metamaterial substrate is placed on top of the metallized metamaterial substrate containing aggregated colloidal gold nanoparticles as a filter for the red blood cells.
3. Next, 10 µL of Phenylalanine dissolved in blood at a concentration <60 mg/dL is pipetted on top of the non-metalized porous substrate.
4. The solution is dried on the sandwiched metamaterials before removing the top filter substrate.
5. Finally, the sample is interrogated with 785 nm laser excitation and Raman instrumentation at a power density of approximately 100 W/cm$^2$.
6. Phenylalanine could be replaced by other analytes of interest as are well known by those skilled in the art.

Since certain changes may be made in the above-described method of using colloidal gold nanoparticles deposited on quartz paper or metamaterial substrates to enable trace level detection of biological materials such as genetic materials using Surface-enhanced Raman Scattering (SERS) without departing from the scope of the invention herein involved, it is intended that all matter contained in the description thereof shall be interpreted as illustrative and not in a limiting sense.

What is claimed is:
1. A method of Surface Enhanced Raman Scattering testing for 1 to 10 ppm analyte using refrigerated 1 mL solutions of prepared colloidal gold nanoparticles having a position of the surface plasmon peak at 540 nm and said analyte testing on substrates in blood comprising:
  mixing 20-30 µL of said prepared colloidal gold nanoparticles with 0.6-1 µL 20 mM NaCl and 5 µL of this mixture is pipetted onto a substrate and allowed to dry;
  placing a non-metalized porous substrate on top of said metallized substrate containing aggregated colloidal gold nanoparticles as a filter for the red blood cells;
  then dissolving 10 µL of said analyte of interest in blood at a concentration <60 mg/dL creating a solution and pipetting said solution on top of the non-metalized porous substrate;
  drying said solution on said sandwiched substrate and non-metalized porous substrate before removing a top filter substrate from said non-metalized porous substrate; and,
  then interrogating the sample with 785 nm laser excitation and Raman instrumentation at a power density of approximately 100 W/cm$^2$.
2. The method of claim 1 wherein the preparation of said prepared colloidal gold nanoparticles is comprising:
  soaking A 250 mL Erlenmeyer flask in a base bath solution;
  rinsing said flask with purified water and creating a solution by adding 200-300 mL of purified water and 0.05 to 0.06 grams HAuCl$_4$;
  preventing any light interaction with gold salt;
  bringing said solution to a boil with magnetic stirring on a hot plate;
  once boiling, the stirring is increased until a vortex is achieved in said solution;
  then adding 0.05 to 0.06 grams sodium citrate to said solution, and continue boiling with stirring for 14 minutes;
  removing said flask from the hot plate and cooling said solution to room temperature;
  cooling said resulting solution containing colloidal gold nanoparticles in a refrigerator; and,
  once cooled, measuring said colloidal gold nanoparticles solution with absorption spectroscopy to confirm the position of the surface plasmon peak at 540 nm.
3. The method of claim 1 wherein said analyte is Phenylalanine.

* * * * *